(12) United States Patent
Nagashio

(10) Patent No.: US 7,889,333 B2
(45) Date of Patent: Feb. 15, 2011

(54) VISUAL INSPECTION SYSTEM FOR CERAMIC BALLS

(75) Inventor: Masaki Nagashio, Kadoma (JP)

(73) Assignee: Amatsuji Steel Ball Mfg. Co., Ltd., Osaka (JP)

( * ) Notice: Subject to any disclaimer, the term of this patent is extended or adjusted under 35 U.S.C. 154(b) by 1081 days.

(21) Appl. No.: 11/589,887

(22) Filed: Oct. 31, 2006

(65) Prior Publication Data

US 2008/0050005 A1 Feb. 28, 2008

(30) Foreign Application Priority Data

Aug. 24, 2006 (JP) ............................. 2006-227385

(51) Int. Cl.
*G01N 21/00* (2006.01)
(52) U.S. Cl. .................... 356/237.1; 356/237.2; 73/593
(58) Field of Classification Search ............. 356/237.1, 356/601, 237.2, 600; 73/593, 642
See application file for complete search history.

(56) References Cited

U.S. PATENT DOCUMENTS

| | | | | |
|---|---|---|---|---|
| 3,572,088 A | * | 3/1971 | Gericke et al. ................. | 73/606 |
| 4,969,361 A | * | 11/1990 | Kawasaki et al. ............. | 73/593 |
| 5,184,513 A | * | 2/1993 | Nishioka et al. ............... | 73/593 |
| 5,285,689 A | * | 2/1994 | Hapstack et al. .............. | 73/623 |
| 6,501,544 B2 | | 12/2002 | Matsuoka | |
| 2002/0135756 A1 | | 9/2002 | Matsuoka | |

FOREIGN PATENT DOCUMENTS

| EP | 0 013 036 | 7/1980 |
|---|---|---|
| JP | 04-070554 | 3/1992 |
| JP | 07-063539 | 3/1995 |
| JP | 10-143641 | 5/1998 |
| JP | 2000-310619 | 11/2000 |
| JP | 2002-277226 | 9/2002 |

\* cited by examiner

*Primary Examiner*—Tarifur Chowdhury
*Assistant Examiner*—Tara S Pajoohi
(74) *Attorney, Agent, or Firm*—Wenderoth, Lind & Ponack, L.L.P.

(57) ABSTRACT

A visual inspection system for ceramic balls inspects flaws in the surface of ceramic balls, and includes an oil tank holding oil, a rotation device for rotating a ceramic ball targeted for inspection that is immersed in the oil in the oil tank, so that detection of the ceramic ball is possible along a meridian, an imaging means for imaging the entire surface of the ceramic ball rotated by the rotation device, an image processing means for image processing an image imaged by the imaging means, and an assessing means for assessing the presence of flaws in the ceramic ball based on image data resulting from the image processing.

8 Claims, 4 Drawing Sheets

VISUAL INSPECTION SYSTEM FOR CERAMIC BALLS

BACKGROUND OF THE INVENTION

This application claims priority under 35 U.S.C. §119(a) to Japanese Patent Application No. 2006-227385 filed in Japan on Aug. 24, 2006, the entire contents of which are hereby incorporated by reference.

The present invention relates to a visual inspection system that assesses the presence of flaws in ceramic balls for use in bearings, ball valves, and the like.

Conventionally, it has commonly been the case with inspection systems for spherical surfaces such as steel balls and the like that the spherical body is generally inspected in air. However, while inspection in air has the advantage of making the spherical body easy to handle, the oil content forms a stain if the spherical surface is not completely degreased by washing, resulting in the spherical body being assessed as defective. Further, the oil content accumulates on the pathway for the balls in the inspection portion, and the adherence of this oil content to the balls may result in a negative assessment. Especially if the spherical body is constructed with an easily corroded metal, there is a possibility of the spherical body rusting when left degreased for a long period of time.

In view of this, the applicant has proposed a system capable of performing surface inspections of a spherical body, without the problem of oil stains such as those described previously, and without the possibility of rusting even with easily corroded metals by making degreasing unnecessary. This system, a main portion of which is shown schematically in FIG. 4, performs surface inspections optically with the spherical body targeted for inspection being immersed in oil. With this surface inspection system, light from a light source 12 is irradiated onto a steel ball 101, being the spherical body targeted for inspection, with the steel ball 101 being immersed in oil and held in place, and the reflected light is received by a light receiving element 13 and converted into electrical signals, after which the presence of flaws in the steel ball 101 is assessed by an assessing portion 11 based on the amount of change in the electrical signals (e.g., see JP 2002-277226A).

However, while optical surface inspection systems that assess the presence of flaws based on the amount of change in electrical signals as described above are ideal for steel balls finished to a mirror surface that are used in common bearings, apparatuses using bearings, ball valves and the like have become faster and more efficient in recent years, and these inspection systems are not effective when it comes to ceramic balls, in demand for their lightness, because even when light is projected the amount of light reflected from a ceramic ball is greatly reduced given that the spherical surface of the ceramic ball is gray or black in color. If the amount of light reflected from the ceramic ball is increased by raising the amount of light from the light source accordingly, the change in signals between flawed and unflawed portions of the spherical surface is reduced because light reflected from objects other than the ceramic ball is also incident on the light receiving element, making it difficult to detect minute flaws. Particularly in the case of ceramic balls, detection was difficult with optical visual inspection systems given the extremely small change in the amount of light reflected from the balls in parts where there were flaws peculiar to ceramics; that is, minute defects such as color unevenness, holes or the like resulting from inclusions in the extreme surface portion. On the other hand, while it is also possible to perform inspections with the naked eye using a microscope, the unavoidable increase in costs due to labor expenses makes this impractical. Also, ceramic balls, unlike steel balls, easily become static electrically charged when friction occurs in the air, attracting small particles of dust in the air, which are viewed as flaws during inspection and lead to erroneous assessments.

SUMMARY OF THE INVENTION

An object of the present invention, which was made in view of the above considerations, is to provide a visual inspection system for ceramic balls that is able to prevent ceramic balls from becoming static electrically charged, and to reliably perform detection of minute flaws and flaws peculiar to ceramics that are difficult to detect with conventional optical inspection systems.

To achieve the above object, a visual inspection system for ceramic balls according to the present invention inspects flaws in the surface of ceramic balls, and includes an oil tank holding oil, a rotation device for rotating a ceramic ball targeted for inspection that is immersed in the oil in the oil tank, so that detection of the ceramic ball is possible along a meridian, an imaging means for imaging the entire surface of the ceramic ball rotated by the rotation device, an image processing means for image processing an image imaged by the imaging means, and an assessing means for assessing the presence of flaws in the ceramic ball based on image data resulting from the image processing.

This configuration is significant for making it possible to scan sequentially along the meridians of a ceramic ball using a rotation device, and being able to prevent dust in the air from adhering to the ceramic ball by having the ceramic ball immersed in oil, thereby enabling highly reliable results to be obtained from the visual inspection of ceramic balls.

Also, the imaging means may be composed of a digital camera that has a lens attached, and a light source that irradiates light onto the ceramic ball.

Further, the digital camera lens and the light source may be disposed in the oil in the oil tank, light from the light source may be irradiated onto the ceramic ball in the oil, and the entire surface of the ceramic ball may be imaged by the digital camera.

The digital camera lens and the light source may also be disposed above the surface of the oil in the oil tank, a transparent body may be disposed on the surface of the oil between the digital camera lens and the ceramic ball, light may be irradiated from the light source onto the ceramic ball in the oil via the transparent body, and the entire surface of the ceramic ball may be imaged by the digital camera via the transparent body.

According to this configuration, the effect of fluctuations in the oil surface can be eliminated by the transparent body. Glass, acrylic or the like can be applied as the transparent body.

Ceramic balls targeted for visual inspection according to the present invention are composed of silicon nitride ($Si_3N_4$), zirconia ($ZrO_2$), alumina ($Al_2O_3$), silicon carbide (SiC), or the like, for example.

The visual inspection system of the present invention detects flaws in a spherical surface, not optically, but by processing images of the spherical surface taken by a digital camera, making it possible to detect minute flaws and flaws peculiar to ceramics that are difficult to detect with optical inspection systems, and thereby enabling the presence of defects in ceramic balls targeted for inspection to be reliably assessed.

Also, it is possible to inspect the entire spherical surface by scanning along the meridians of a ceramic ball using a rotation device as described above. Further, inspection of ceramic balls in oil is made possible by installing the rotation device in the oil, thereby enabling the elimination of processes to wash, degrease and dry the balls prior to inspection. Although ceramic balls in particular easily become static electrically charged, giving rise to the possibility of erroneous assessments caused by dust adhering in air, this can be suppressed by performing the inspection in oil.

DETAILED DESCRIPTION OF THE INVENTION

Embodiments of the present invention are described below based on the drawings.

Figure 1:
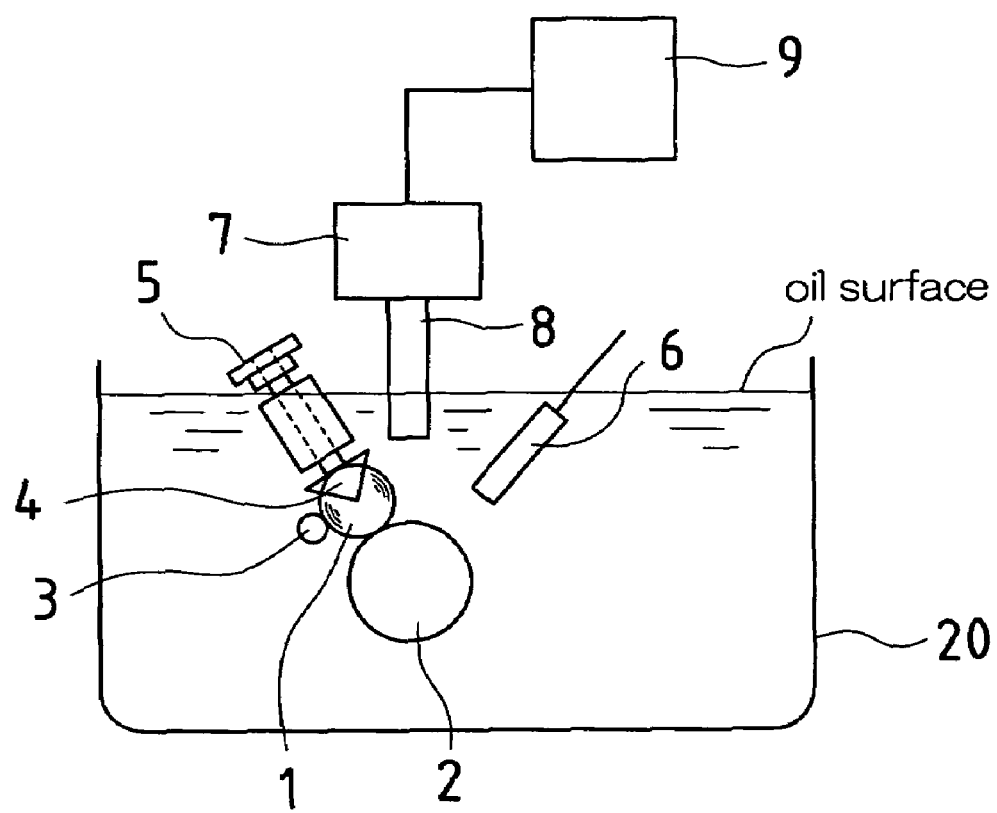
FIG. 1 schematically shows a main portion of an inspection system according to an embodiment of the present invention.

FIG. 1 schematically shows a main portion of a visual inspection system according to one embodiment of the present invention. A ceramic ball 1 targeted for inspection is immersed in oil held in an oil tank 20 by a drive roller 2, a support roller 3, and two conical control rollers 4 that form a pair, and fixed in a prescribed position. An eccentric helical gear 5 is provided at the other end of each of the control rollers 4.

A digital camera 7 for imaging the entire spherical surface is provided so as to be fixed in a prescribed position, and a lens 8 provided in this digital camera 7 is partially immersed in oil. A light source 6 for irradiating light onto the ceramic ball 1 is provided in oil in a vicinity of the ceramic ball 1. A personal computer 9 assesses the presence of defects in the ceramic ball 1 targeted for inspection by performing prescribed processing on surface images of the ceramic ball 1 taken by the digital camera 7.

Figure 2:
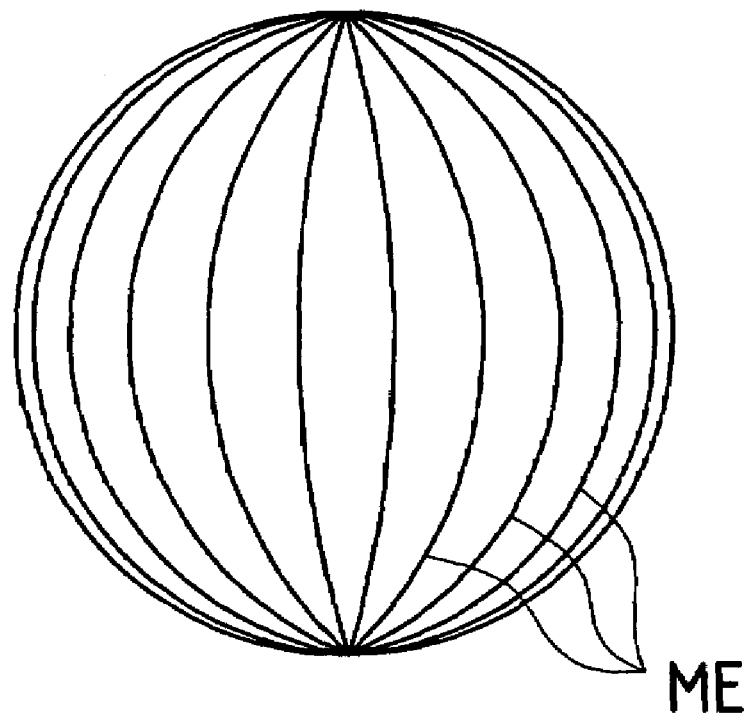
FIG. 2, which is for illustrating the operation of the inspection system according to an embodiment of the present invention, shows an inspection trajectory on a spherical body.

With a visual inspection system having the above configuration, firstly a ceramic ball 1 set on the drive roller 2 rotates due to the drive roller 2 being rotated, and the control rollers 4 also rotate due to the rotation of this ceramic ball 1. A twist is given to the ceramic ball 1 at this time by the eccentricity of each of the eccentric helical gears 5, and as a result of the rotation along the meridians ME given to the ceramic ball 1 in relation to the lens 8 of the digital camera 7, as shown in FIG. 2, the entire spherical surface of the ceramic ball 1 is imaged along the meridians ME.

The present embodiment is thus configured so that prescribed processing is performed on images taken as a result of using the digital camera 7 to assess the presence of flaws on the entire surface of the ceramic ball 1.

Note that the lens 8 attached to the digital camera 7 can be easily made to cope with detecting minute flaws by appropriately changing the lens magnification.

Figure 3:
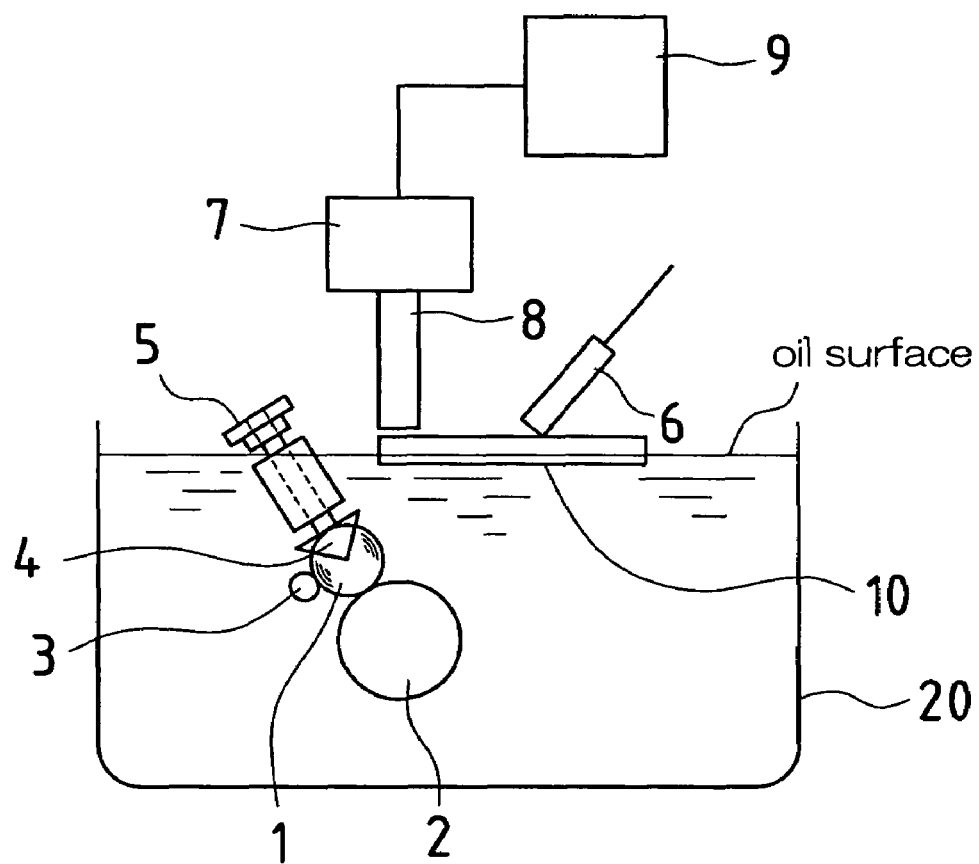
FIG. 3 schematically shows a main portion of an inspection system according to another embodiment of the present invention.
Figure 4:
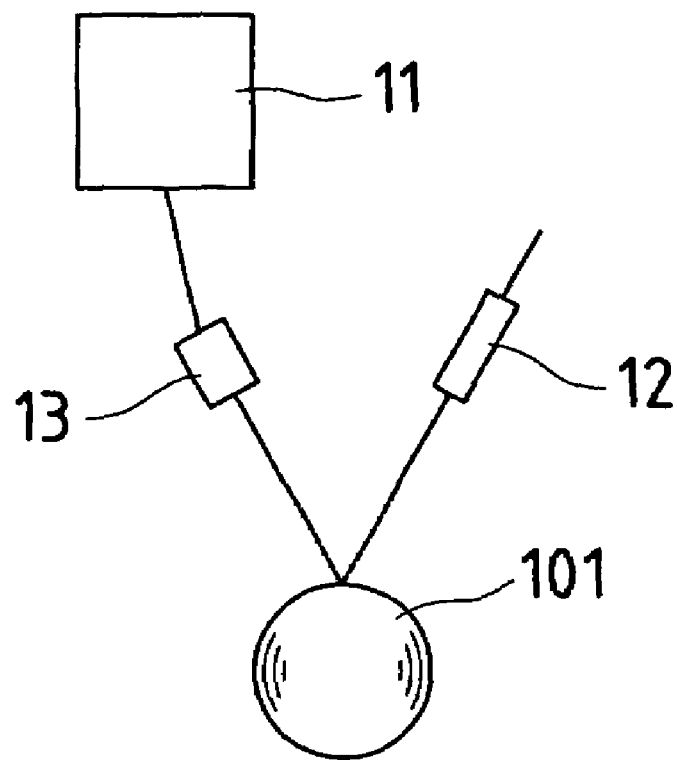
FIG. 4 schematically shows a main portion of a conventional inspection system.

Although the above embodiment was described in terms of the camera lens 8 and the light source 6 being immersed in oil as shown in FIG. 1, the camera lens 8 and the light source 6 may be disposed above the oil surface without necessarily being immersed in the oil, as shown in FIG. 3. In this case, a transparent body 10 such as glass or acrylic needs to be disposed on the surface of the oil between the camera lens 8 and the ceramic ball 1 targeted for inspection in order to eliminate the affect of fluctuations in the oil surface. The images taken by the digital camera 7 are thus effective, with clear images being obtained that are not affected by fluctuations in the oil surface.

With the present embodiment, inspection in oil is made possible in particular by the drive roller 2, the control rollers 4, and the support roller 3 that are installed in the oil. Processes to wash, degrease, and dry the balls before inspection, as with conventional technology, are thus unnecessary, enabling these processes to be eliminated, and making this configuration efficient and economical. Further, because of the possibility of erroneous assessments with ceramic balls given that, unlike steel balls, they easily become static electrically charged, and dust and the like readily adhere to the balls in air due to the static electricity, the above configuration is also superior in terms of being able to avoid this.

With the present embodiment, minute objects preferably are eliminated from the oil by using micro filters to filter the oil.

As described above, the visual inspection system of the present embodiment, unlike conventional optical inspection systems, processes images of spherical surfaces taken with a digital camera, enabling minute flaws and particularly flaws peculiar to ceramic balls to be detected, and also has excellent usability in terms of the anticipation of future demand.

INDUSTRIAL APPLICABILITY

The visual inspection system of the present invention is also applicable in the visual inspection of balls, other than ceramic balls, that easily become static electrically charged.

The present invention can be implemented in other forms without departing from the gist or essential characteristics thereof. The above embodiments are thus considered in all respects as illustrative and not limiting. The scope of the invention is indicated by the appended claims, and is not restricted by the forgoing description. Further, all modifications and changes that come within the range of equivalency of the claims are embraced within the scope of the invention.

What is claimed is:

1. A visual inspection system for ceramic balls that inspects flaws in a surface of ceramic balls, the system comprising:
   an oil tank for holding oil;
   a rotation device for rotating a ceramic ball targeted for inspection that is immersed in the oil in the oil tank, said rotation device including a drive roller, a pair of control rollers, and a support roller which fix the ceramic ball in a prescribed position in the oil, wherein each of said control rollers is equipped with an eccentric helical gear and the ceramic ball is rotated by the eccentric helical gears so that detection of the ceramic ball is possible along a meridian;
   imaging means for imaging an entire surface of the ceramic ball rotated by the rotation device, said imaging means including a light source for irradiating light onto the ceramic ball and a digital camera having a lens;
   image processing means for image processing an image taken by the imaging means; and
   assessing means for assessing a presence of flaws in the ceramic ball based on image data resulting from the image processing.

2. The visual inspection system for ceramic balls according to claim 1, wherein the digital camera lens and the light source are disposed in the oil in the oil tank, the light source is arranged to irradiate light onto the ceramic ball in the oil, and the entire surface of the ceramic ball is imaged by the digital camera.

3. The visual inspection system for ceramic balls according to claim 1, further comprising a transparent body disposed on the surface of the oil between the digital camera lens and the ceramic ball,
wherein the digital camera lens and the light source are disposed above a surface of the oil in the oil tank, the light source is arranged to irradiate light onto the ceramic ball in the oil through the transparent body, and the entire surface of the ceramic ball is imaged by the digital camera via the transparent body.

4. The visual inspection system for ceramic balls according to claim 1, further comprising a transparent body disposed on the surface of the oil between the digital camera lens and the ceramic ball,
wherein the transparent body has a first surface and a second surface opposed to the first surface, and the transparent body is arranged such that the first surface is above the surface of the oil and the second surface is below the surface of the oil to eliminate the affect of fluctuations in the surface of the oil,
wherein the digital camera lens and the light source are disposed above a surface of the oil in the oil tank, the light source is arranged to irradiate light onto the ceramic ball in the oil through the transparent body, and the entire surface of the ceramic ball is imaged by the digital camera via the transparent body.

5. A visual inspection system for ceramic balls that inspects flaws in a surface of ceramic balls, the system comprising:
an oil tank for holding oil;
a rotation device for rotating a ceramic ball targeted for inspection that is immersed in the oil in the oil tank, said rotation device including a drive roller, a pair of control rollers, and a support roller which fix the ceramic ball in a prescribed position in the oil, wherein each of said control rollers is equipped with an eccentric helical gear and the ceramic ball is rotated by the eccentric helical gears so that detection of the ceramic ball is possible along a meridian;
an imaging device which takes an image of an entire surface of the ceramic ball rotated by the rotation device, said imaging device including a light source for irradiating light onto the ceramic ball and a digital camera having a lens;
an image processor which processes an image taken by the imaging device; and
an assessing device which assesses a presence of flaws in the ceramic ball based on image data resulting from the image processing.

6. The visual inspection system for ceramic balls according to claim 5, wherein the digital camera lens and the light source are disposed in the oil in the oil tank, the light source is arranged to irradiate light onto the ceramic ball in the oil, and the entire surface of the ceramic ball is imaged by the digital camera.

7. The visual inspection system for ceramic balls according to claim 5, further comprising a transparent body disposed on the surface of the oil between the digital camera lens and the ceramic ball,
wherein the digital camera lens and the light source are disposed above a surface of the oil in the oil tank, the light source is arranged to irradiate light onto the ceramic ball in the oil through the transparent body, and the entire surface of the ceramic ball is imaged by the digital camera via the transparent body.

8. The visual inspection system for ceramic balls according to claim 5, further comprising a transparent body disposed on the surface of the oil between the digital camera lens and the ceramic ball,
wherein the transparent body has a first surface and a second surface opposed to the first surface, and the transparent body is arranged such that the first surface is above the surface of the oil and the second surface is below the surface of the oil to eliminate the affect of fluctuations in the surface of the oil,
wherein the digital camera lens and the light source are disposed above a surface of the oil in the oil tank, the light source is arranged to irradiate light onto the ceramic ball in the oil through the transparent body, and the entire surface of the ceramic ball is imaged by the digital camera via the transparent body.

* * * * *